(12) United States Patent
Warnock

(10) Patent No.: US 9,523,633 B1
(45) Date of Patent: Dec. 20, 2016

(54) NONDESTRUCTIVE PROOF LOADING OF HONEYCOMB PANELS

(71) Applicant: Space Systems/Loral, LLC, Palo Alto, CA (US)

(72) Inventor: Richard Warnock, Mountain View, CA (US)

(73) Assignee: Space Systems/Loral, LLC, Palo Alto, CA (US)

( * ) Notice: Subject to any disclaimer, the term of this patent is extended or adjusted under 35 U.S.C. 154(b) by 109 days.

(21) Appl. No.: 14/448,744

(22) Filed: Jul. 31, 2014

(51) Int. Cl.
*G01N 19/04* (2006.01)
*G01N 3/08* (2006.01)

(52) U.S. Cl.
CPC ............... *G01N 19/04* (2013.01); *G01N 3/08* (2013.01)

(58) Field of Classification Search
CPC ............. G01N 19/04; G01N 3/08; G01N 3/10
See application file for complete search history.

(56) References Cited

U.S. PATENT DOCUMENTS

| 2,694,924 | A | 11/1954 | Matlock et al. |
| 4,491,014 | A | 1/1985 | Seiler |
| 4,567,758 | A | 2/1986 | Fisher et al. |
| 6,386,027 | B1 * | 5/2002 | Westin ............... G01N 3/08 73/159 |
| 7,258,760 | B2 | 8/2007 | Yamaguchi et al. |
| 8,349,104 | B2 | 1/2013 | Vontell |
| 2012/0193015 | A1 * | 8/2012 | Segal ............... C08G 59/4207 156/182 |

OTHER PUBLICATIONS

ASTM Designation: C297/C297M-04, "Standard Test Method for Flatwise Tensile Strength of Sandwich Constructions", May 2004.*
Callus et al., "F-111 Adhesive Bonded Repair Assessment Program (FABRAP)—Phase I Testing, Preliminary Results)", Unclassified, Australian Government Department of Defence, Defence Science and Technology Organization, Air Vehicles Division, DSTO-TN-1024, Aug. 2011, 79 pages.
Cen, "Aerospace Series—Non-metallic materials—Structural adhesives—Test method—Part 4: Metal-honeycomb core flatwise tensile test", European Committee for Standardization, EN 2243-4:2005(E), 2005, 14 pages.

(Continued)

*Primary Examiner* — Paul West
(74) *Attorney, Agent, or Firm* — Weaver Austin Villeneuve & Sampson LLP

(57) ABSTRACT

Techniques for testing whether a bond strength between a faceskin of a panel and a core of the panel exceeds a threshold value are disclosed. The testing includes: adhering a first surface of a sacrificial layer to a pull stub of a flatwise tensile (FWT) test apparatus by way of a first adhesive interface; adhering the second surface of the sacrificial layer to the panel faceskin by way of a second adhesive interface; operating the FWT test apparatus so as to gradually increase a FWT load on the faceskin; terminating the test upon the first to occur of separation of any one or more of the first adhesive interface, the second adhesive interface, the sacrificial layer and separation of the faceskin from the core; and determining that the bond strength exceeds the threshold value when separation of the faceskin from the core is not the first to occur.

18 Claims, 6 Drawing Sheets

(56) References Cited

OTHER PUBLICATIONS

Lee et al., "Assessment of Adhesive Bonded Repairs, A Thesis Submitted in Fulfillment of the Requirements for the Degree of Master of Engineering", School of Aerospace, Mechanical and Manufacturing Engineering, College of Science, Engineering and Health, RMIT University, Mar. 2013, 173 pages.

"PATTI Pneumatic Adhesion Tensile Testing Instrument", QUANTUM Series, Operator's Manual (Ditigital Model), retrieved on Oct. 27, 2014 from Internet at http://www.semicro.org/Quantum%20Digital%20Manual.pdf, 32 pages.

* cited by examiner

*Exploded isometric view*

*View A-A*

*View B-B*

NONDESTRUCTIVE PROOF LOADING OF HONEYCOMB PANELS

TECHNICAL FIELD

This invention relates generally to spacecraft structural testing, and, more particularly, to testing the bond strength of faceskins of honeycomb core panels.

BACKGROUND OF THE INVENTION

The assignee of the present invention manufactures and deploys spacecraft for, inter alia, communications and broadcast services from geostationary orbit. During launch, such spacecraft are enclosed within a launch vehicle payload fairing that experiences depressurization from an initial pressure of nominally one atmosphere (approximately 14.7 PSIA) to a near vacuum condition within a time period of about two minutes. To safely accommodate this pressure change, the spacecraft design must include provisions for safely venting of air from interior volumes of the spacecraft and spacecraft components into the launch vehicle payload fairing.

Large structural components of a spacecraft include spacecraft equipment and solar array panels and structural panels that may be in the range of 50 square feet surface area, or greater. Referring to FIG. 1, an exploded isometric view of an example structural panel 100 is illustrated. Panel 100 includes a honeycomb core 110 sandwiched between panel faceskins 120. The panel faceskins 120 may be formed from aluminum or a carbon composite material, for example, and have a cell wall thickness, typically, of less than 0.01 inches. The panel faceskins 120 may be adhered to a honeycomb core 110 by epoxy adhesive or other adhesive bond, for example.

Referring now to views A-A and B-B of FIG. 1, each cell in the honeycomb core is intended to be vented (by slitting or perforating, for example) to permitted air to escape during launch as the spacecraft leaves the earth's surface and experiences a depressurization from approximately one atmosphere of pressure to the vacuum of space.

In practice, however, it has been found that some cells of an as-fabricated honeycomb panel, which may typically include several thousand cells, may exhibit manufacturing defects as a result of which the defective cells fail to comply with the design intent of providing safe venting means. Such manufacturing flaws are difficult to completely prevent and may be difficult to detect by conventional inspection or nondestructive test techniques. A consequence of such undetected flaws can include explosive rupture of the panel, and resulting damage to spacecraft functional systems.

The bond strength between panel faceskin and core may vary from panel to panel and within a given flight panel. To mitigate the risk of damage in the event that normal venting of the honeycomb core during launch ascent is not achieved, it is desirable that the bond strength be sufficient to withstand a pressure differential of one atmosphere or more. Bond strength between panel faceskin and core of a flight panel is ordinarily estimated by way of destructively testing coupon samples that are co-manufactured with the flight panel. However, such coupon testing has been problematic because coupon bond strength may not accurately correlate with bond strength of the flight panel, particularly the weakest point of the flight panel.

As a result, an improved approach to bond strength testing of flight honeycomb core panels is desirable.

SUMMARY

The present disclosure contemplates improved techniques for testing bond strength testing of flight honeycomb core panels.

In an implementation, a method includes testing whether a bond strength between a faceskin of a panel and a core of the panel exceeds a threshold value. The testing includes: adhering a first surface of a sacrificial layer to a pull stub of a flatwise tensile (FWT) test apparatus by way of a first adhesive interface, the sacrificial layer including a second surface opposite to the first surface; adhering the second surface of the sacrificial layer to the panel faceskin by way of a second adhesive interface; operating the FWT test apparatus so as to gradually increase a FWT load on the faceskin; terminating the test upon the first to occur of either: condition (i), separation of any one or more of the first adhesive interface, the second adhesive interface and the sacrificial layer; or condition (ii), separation of the faceskin from the core; and determining that the bond strength exceeds the threshold value when condition (i) is the first to occur.

In some implementations, the FWT test apparatus may be a pneumatic adhesion tensile testing instrument.

In some implementations, the sacrificial layer may a double sided tape. The double-sided tape may have a modulus of less than 500. The double-sided tape may have a modulus of approximately 75.

In some implementations, the panel may be a spacecraft solar array panel or equipment panel.

In some implementations, the faceskin may be aluminum or carbon composite.

In some implementations, the pull stub may have a test article interface area defined by a perimeter and the pull stub may be configured to have a first stiffness proximate to the perimeter and a second stiffness in a central region of the test article interface area, the first stiffness being substantially less than the second stiffness.

In some implementations, the pull stub may be configured to have a first thickness proximate to the perimeter and a second thickness in a central region of the test article interface area, the first thickness being substantially less than the second thickness.

In an implementation, an apparatus includes: a flatwise tensile (FWT) test device, the FWT test device including a pull stub and a sacrificial layer. A first surface of the sacrificial layer is adhered to the pull stub by way of a first adhesive interface, and the FWT test device is configured to determine whether a bond strength between a faceskin of a panel and a core of the panel exceeds a threshold value by: adhering a second surface of the sacrificial layer to the faceskin by way of a second adhesive interface, the second surface being opposite to the first surface; operating the FWT test apparatus so as to gradually increase a FWT load on the faceskin; and terminating the test upon the first to occur of either: condition (i), separation of any one or more of the first adhesive interface, the second adhesive interface and the sacrificial layer; or condition (ii), separation of the faceskin from the core; and determining that the bond strength exceeds the threshold value when condition (i) is the first to occur.

BRIEF DESCRIPTION OF THE DRAWINGS

Features of the invention are more fully disclosed in the following detailed description of the preferred embodiments, reference being had to the accompanying drawings, in which.

Figure 1:
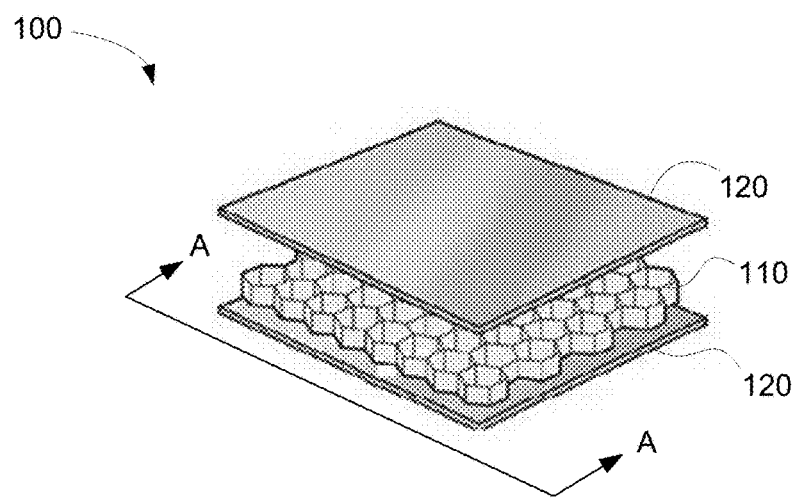
FIG. 1 illustrates an example of a spacecraft structural component to which implementations of the invention may be applied.
Figure 1:
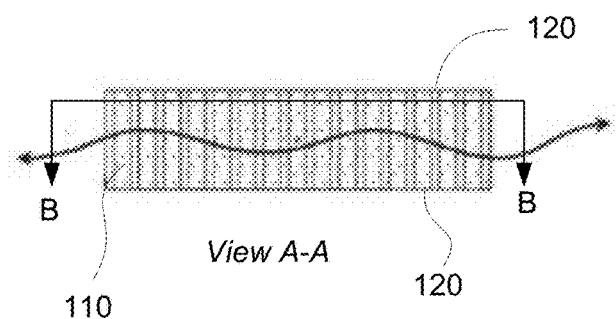
Figure 1:
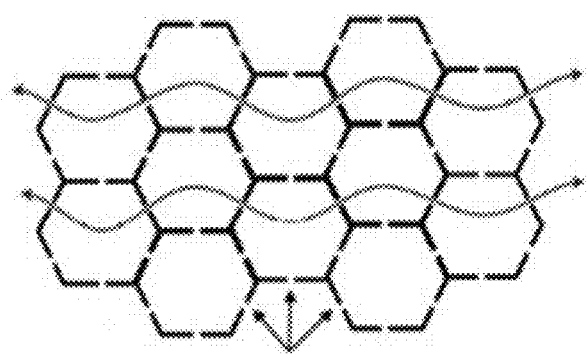

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

DETAILED DESCRIPTION

Specific examples of embodiments will now be described with reference to the accompanying drawings. This invention may, however, be embodied in many different forms, and should not be construed as limited to the embodiments set forth herein. Rather, these embodiments are provided so that this disclosure will be thorough and complete, and will fully convey the scope of the invention to those skilled in the art.

It will be understood that when an element is referred to as being "connected" or "coupled" to another element, it can be directly connected or coupled to the other element, or intervening elements may be present. It will be understood that although the terms "first" and "second" are used herein to describe various elements, these elements should not be limited by these terms. These terms are used only to distinguish one element from another element. As used herein, the term "and/or" includes any and all combinations of one or more of the associated listed items. The symbol "/" is also used as a shorthand notation for "and/or".

Figure 2:
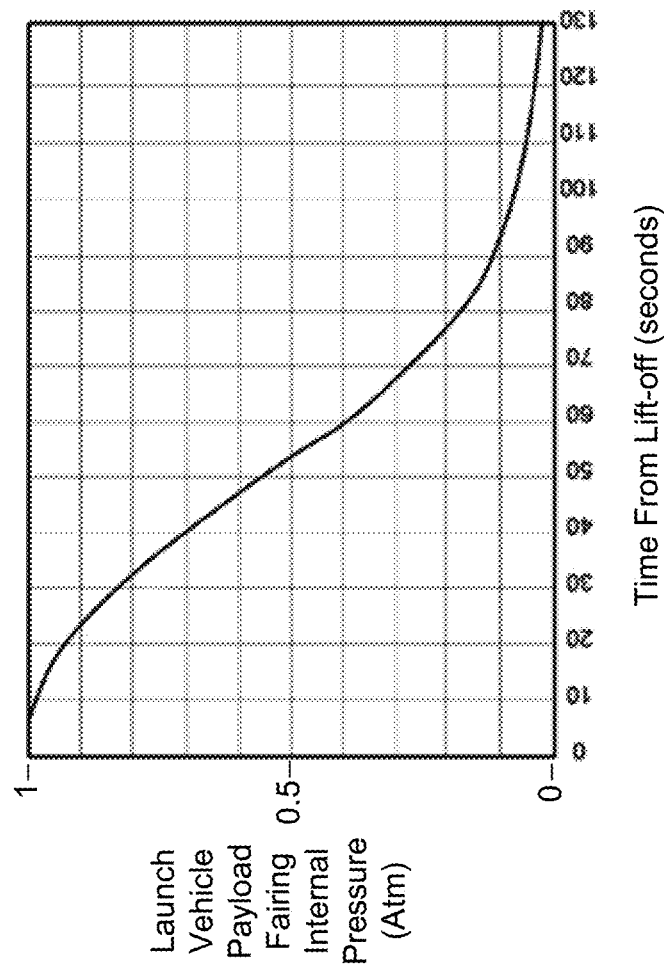
FIG. 2 illustrates an example of a pressure profile within a launch vehicle payload fairing during launch vehicle ascent.

The presently disclosed techniques permit validation, by nondestructive ground test, that the bond strength between panel faceskin and honeycomb core of a flight panel meets or exceeds a specified criterion. In some implementations, the criterion may be related to the internal pressure that may develop within the panel as a result of launch vehicle assent plus a factor of safety. Referring now to FIG. 2, an example of a pressure profile within a launch vehicle payload fairing during launch vehicle ascent is illustrated. In the illustrated example, pressure within the payload fairing decreases from one atmosphere to approximately a vacuum in approximately 130 seconds. In the event that normal venting of the honeycomb core during launch ascent is not achieved, the pressure differential between the panel interior and exterior may be as high as one atmosphere.

According to the presently disclosed techniques, compatibility of faceskin bond strength with a pressure profile such as the one illustrated in FIG. 2 is demonstrated by a nondestructive bond strength test. In some implementations, a flatwise tensile (FWT) test device is employed. A suitable test apparatus may be adapted for nondestructive testing as detailed below from a pneumatic adhesion tensile testing instrument similar to the type available from, for example, the SEMicro Division of M.E. Taylor Engineering, Inc., of Rockville Md.

Figure 3:
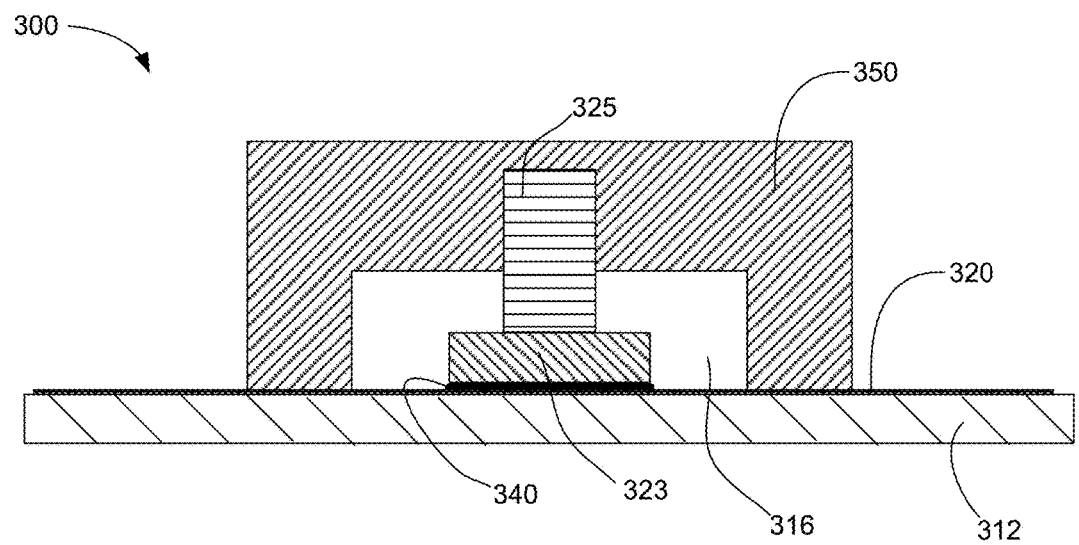
FIG. 3 illustrates an example of a pneumatic flatwise tensile test (FWT) device.

It should be noted that, in the absence of the present teachings, FWT test devices are employed for destructive testing of various test articles. For example, as disclosed in U.S. Pat. No. 4,491,014 to Seiler, Jr. (hereinafter, "Seiler", incorporated herein by reference in its entirety), and illustrated in FIG. 3, a pneumatic FWT test device 300 may destructively test the adhesive bond of a lamina 320 to a substrate 312. A pull stub 323 is bonded by way of an adhesive 340 to the lamina 320. The pull stub may include or be structurally secured to a threaded shank 325 which may engage a threaded bore in piston 350. The lamina 320 may be a paint layer or similar thin coating applied to the substrate 312. An ultimate strength of the bond between lamina 320 and substrate 312 may be determined by increasing a tensile load on the pull stub, until the bond breaks. Typically, the tensile load is increased by increasing pneumatic pressure within chamber 316. By measuring the pressure within chamber 316 at which the bond breaks, the bond strength between lamina 320 and substrate 312 may be determined. According to Seiler, the adhesive 340, typically an epoxy glue, must provide a bond between pull stub 323 and lamina 320 that is stronger than the bond between the lamina 320 and the substrate 312.

Figure 4:
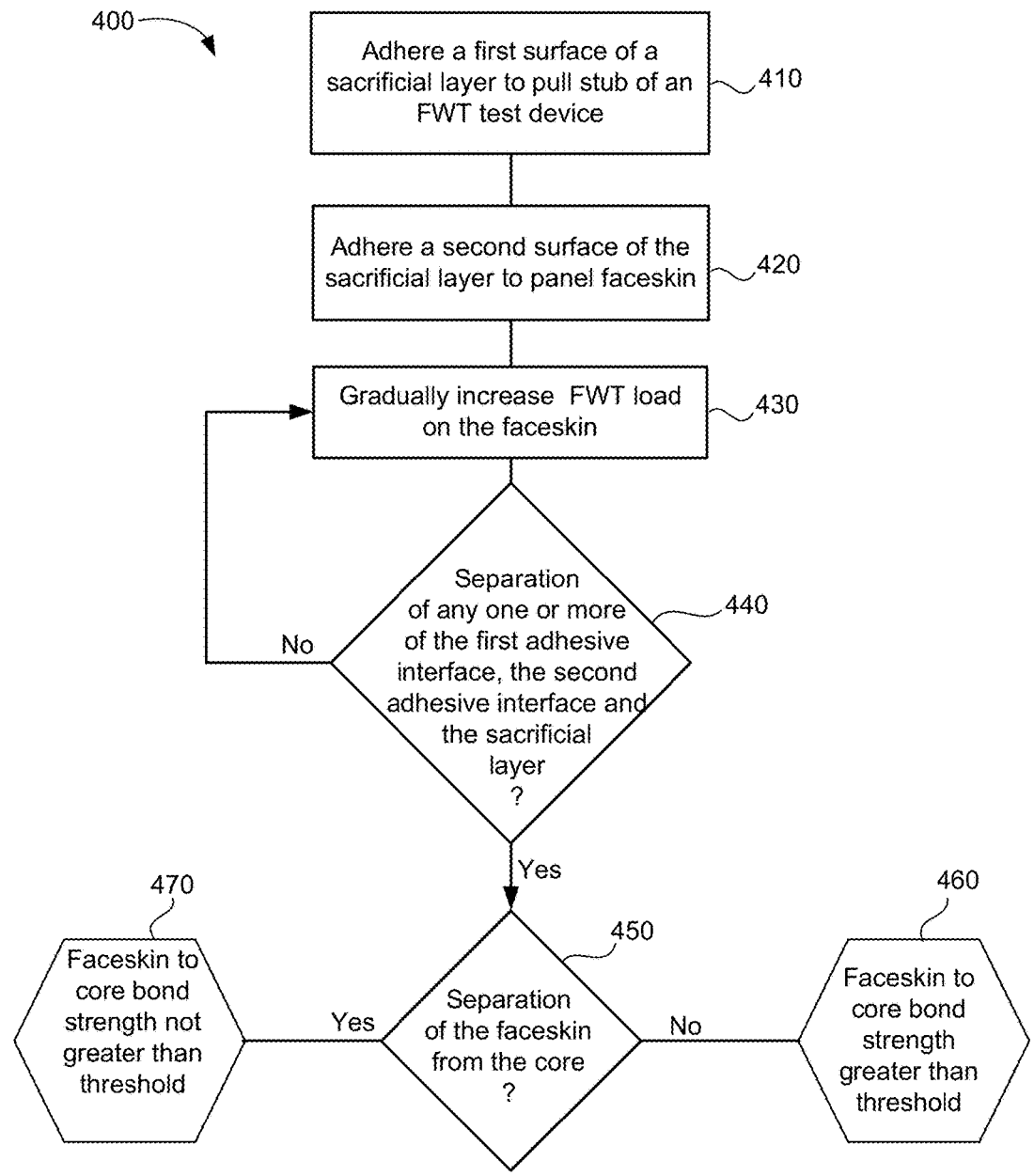
FIG. 4 illustrates an example implementation of a nondestructive test technique according to some implementations.

According to the presently disclosed techniques, testing to verify that a bond strength between a panel faceskin and a core exceeds a minimum acceptable FWT strength (the "threshold value") may be accomplished using an FWT test apparatus in the manner illustrated in FIG. 4. A method 400 may start, at block 410 by adhering a first surface of a sacrificial layer to a pull stub of the FWT test device. The sacrificial layer may be a double-sided tape, for example. In some implementations the double-sided tape may be a foam adhesive tape that fails under a transverse tensile load of less than 40 PSI. The double-sided tape may be configured to be removable from the faceskin (by peeling, for example) without damaging the faceskin. In some implementations, the adhesion strength of at least one side of the double-sided tape may be selected such that it is greater than a first specified value and less than a second specified value. The first specified value may be related to the threshold value for FWT strength of the bond between the faceskin and the core. The second specified value may be related to the maximal FWT load that the faceskin may be expected to sustain without damage. In some implementations, margin factors may be applied to one or both of the minimum acceptable FWT strength and the maximal FWT load that the faceskin may be expected to sustain without damage. In an embodiment, for example, the sacrificial layer has been designed to reliably survive an FWT load of no less than 25 PSI and to reliably break at an FWT load of no greater than 50 PSI.

Figure 5:
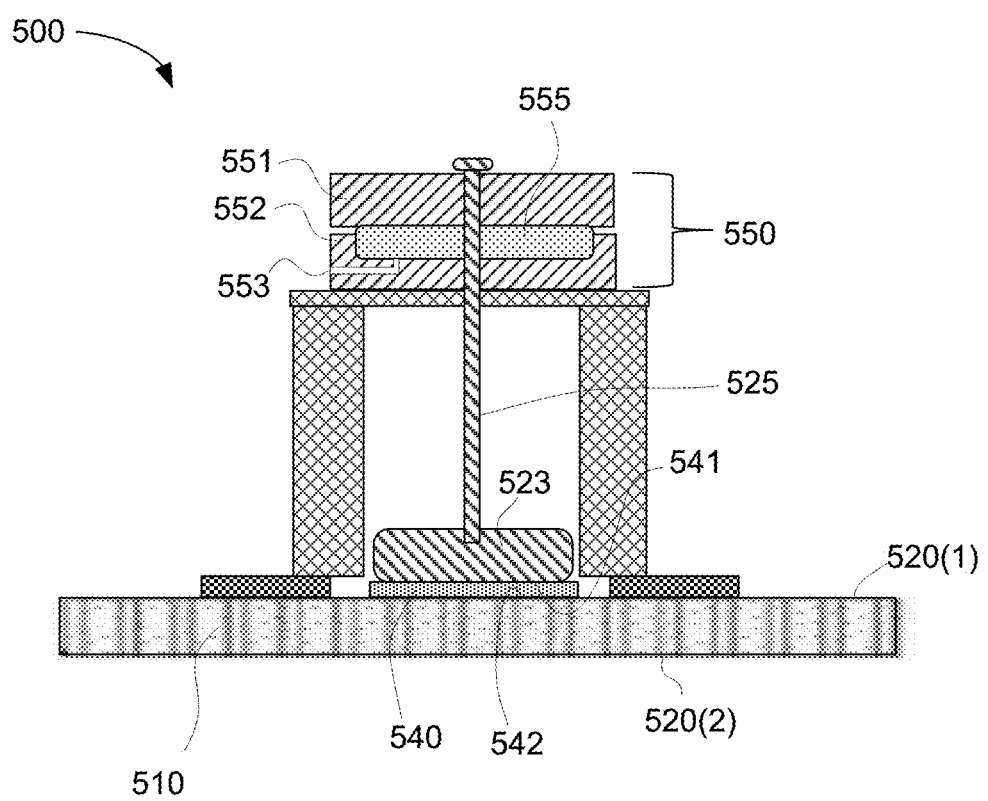
FIG. 5 illustrates an example of a FWT test device for nondestructive testing according to some implementations.

Block 410, in some implementations may include, referring now to FIG. 5, adhering a first surface 541 of double back foam adhesive 540 to a pull stub 523 of a FWT test device 500 by way of a first adhesive interface between the first surface 541 and the pull stub 523. The FWT test device 500 may include the pneumatic adhesion tensile testing instrument test apparatus referenced above.

Referring again to FIG. 4, method 400 may continue, at block 420, by adhering a second surface of the sacrificial layer, to the panel faceskin.

Block 420, in some implementations may include, referring again to FIG. 5, adhering a second surface 542 of the sacrificial layer 540 to a faceskin 520(1) of an equipment panel by way of a second adhesive interface between the second surface 542 and the faceskin 520(1). In the illustrated implementation, the equipment panel includes honeycomb core 510 sandwiched between the first faceskin 520(1) and a second faceskin 520(2).

Referring again to FIG. 4, method 400 may continue, at block 430, by gradually increasing a FWT load on the panel faceskin.

Block 430, in some implementations may include, referring again to FIG. 5, gradually increasing the FWT load by pressurizing piston arrangement 550. In the illustrated implementation piston arrangement 550 includes an upper plate 551, lower plate 552 and gasket 555. Gasket 555, which may be composed of silicon or similar elastomeric material, is disposed between upper plate 551 and lower plate 552 so as to form a sealed plenum into which pressurizing fluid may be introduced by way of input 553. The pressurizing fluid may be a gas or hydraulic fluid, for example. The pressurizing fluid may be supplied to inlet 551 such that pressure is gradually increased within the sealed plenum, as a result of which a gradually increasing lifting force is exerted against upper plate 551. The lifting force is transferred by way of shank 525 to pull stub 523 which in turn imparts a tensile load across sacrificial layer 540.

Referring again to FIG. 4, at block 440, a determination may be made as to whether or not a separation of any one or more of the first adhesive interface, the second adhesive interface, and the sacrificial layer has occurred. The determination at block 440 may be made frequently or in a substantially continuous manner. If the determination at block 440 is that a separation has not occurred then the method returns to block 430. On the other hand, if the determination at block 440 is that a separation has occurred that the method may proceed to block 450, as described hereinbelow.

At block 450, a determination may be made as to whether or not separation of the faceskin from the core has occurred. The determination may be made on the basis of a visual inspection of the panel and/or of the sacrificial layer, for example. If the determination at block 450 is that separation of the faceskin from the core has occurred, it may be determined at block 470 that the faceskin and the core bond strength does not exceed the threshold value. On the other hand, if the determination at block 450 is that separation of the faceskin from the core has not occurred, it may be determined at block 460 at the faceskin and the core bond strength exceeds the threshold value.

In accordance with the presently disclosed techniques, and referring again to FIG. 5, an FWT test procedure may be terminated upon separation of the faceskin 520(1) from the honeycomb core 510, or separation of the sacrificial layer 540, whichever comes first. It will be understood that separation of sacrificial layer 540 may occur by way of either a break in the first adhesive interface between the sacrificial layer 540 and the pull stub 523, or a break in the second adhesive interface between sacrificial layer 540 and the faceskin 520(1), or by way of failure of the sacrificial layer 540 itself. For example, where the sacrificial layer 540, is a double back foam tape adhesive, a strength of each of the first adhesive interface and the second adhesive interface may be greater than the strength of the foam tape material.

By judicious selection of the characteristics of the sacrificial layer 540, the FWT test device 500 may be configured such that separation of sacrificial layer 540 occurs only at a tensile load that is (i) greater than the minimum acceptable FWT strength of the bond between the faceskin and the core and (ii) less than the maximal FWT load that the faces skin may be expected to sustain without damage.

Figure 6:
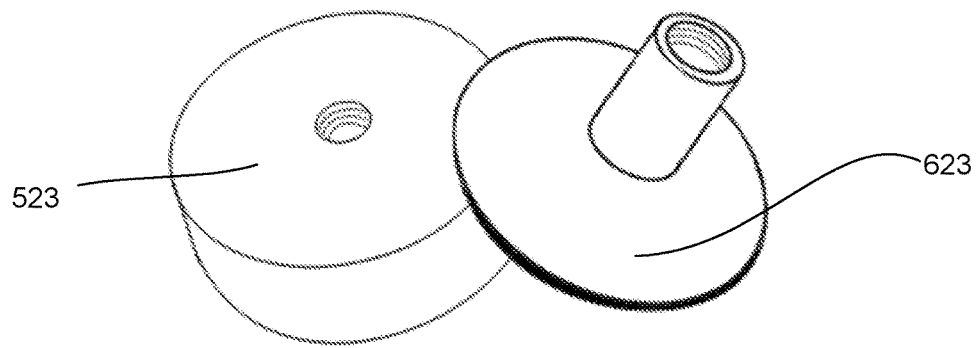
FIG. 6 compares two examples of a pull stub of a FWT test device.
Figure 7:
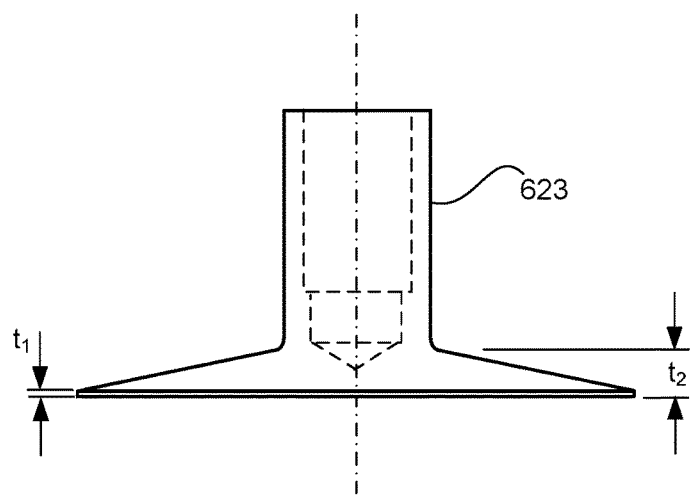
FIG. 7 illustrates an example of a pull stub of an FWT device according to an implementation.

It is desirable to provide approximately uniform stress distribution across the surface area within which the pull stub interfaces with the faceskin (test article interface area). In some implementations, this may be accomplished by configuring the pull stub with a tapered thickness, wherein the thickness and stiffness of the pull stub near a perimeter of the interface area is substantially smaller than in a central region. An example implementation is illustrated in FIGS. 6 and 7. FIG. 6 compares a conventional pull stub 523 with a tapered pull stub 623. FIG. 7 illustrates a specific implementation of a tapered pull stub where a first thickness $t_1$, proximate to the perimeter of the interface area, is substantially less like than a second thickness $t_2$ near the central region.

More uniform stress distribution may also be provided by selection of adhesive layer having relatively low modulus. For example a modulus of less than 500 PSI is within the contemplation of the present disclosure. Advantageously, the modulus may be approximately 75 PSI.

Thus, improved techniques for testing a spacecraft component for compatibility with a depressurization profile associated with a launch vehicle ascent have been disclosed. It will be appreciated that the presently disclosed techniques may be implemented as part of nondestructive acceptance test program executed on flight hardware. As a result, a need to perform coupon testing of co-manufactured non-flight coupons may be avoided. Moreover, a risk that such co-manufactured coupons may not accurately correlate with bond strength of the flight panel is avoided.

The foregoing merely illustrates principles of the invention. It will thus be appreciated that those skilled in the art will be able to devise numerous systems and methods which, although not explicitly shown or described herein, embody said principles of the invention and are thus within the spirit and scope of the invention as defined by the following claims.

What is claimed is:
1. A method comprising:
testing whether a bond strength between a faceskin of a panel and a core of the panel exceeds a threshold value, the testing including:
adhering a first surface of a sacrificial layer to a pull stub of a flatwise tensile (FWT) test apparatus by way of a first adhesive interface, the sacrificial layer including a second surface opposite to the first surface;
adhering the second surface of the sacrificial layer to the panel faceskin by way of a second adhesive interface;
operating the FWT test apparatus so as to gradually increase a FWT load on the faceskin;
terminating the test upon the first to occur of either: condition (i), separation of any one or more of the first adhesive interface, the second adhesive interface and the sacrificial layer; or condition (ii), separation of the faceskin from the core; and
determining that the bond strength exceeds the threshold value when condition (i) is the first to occur, wherein the bond strength is expected to exceed a specified maximal FWT load; and the sacrificial layer is configured such that condition (i) occurs only at a tensile load that is greater than the threshold value and less than the maximal FWT load.

2. The method of claim 1, wherein the FWT test apparatus is a pneumatic adhesion tensile testing instrument.

3. The method of claim 1, wherein the sacrificial layer is a double sided tape.

4. The method of claim 3, wherein the double-sided tape has a modulus of less than 500.

5. The method of claim 3, wherein the double-sided tape has a modulus of approximately 75.

6. The method of claim 1, wherein the panel is a spacecraft solar array panel or equipment panel.

7. The method of claim 1, wherein the faceskin is aluminum or carbon composite.

8. The method of claim 1, wherein the pull stub has a test article interface area defined by a perimeter and the pull stub is configured to have a first stiffness proximate to the perimeter and a second stiffness in a central region of the test article interface area, the first stiffness being substantially less than the second stiffness.

9. The method of claim 1, wherein the pull stub is configured to have a first thickness proximate to the perimeter and a second thickness in a central region of the test article interface area, the first thickness being substantially less than the second thickness.

10. An apparatus comprising:
a flatwise tensile (FWT) test device, the FWT test device including a pull stub and a sacrificial layer wherein:
the FWT test device is configured to determine whether a bond strength between a faceskin of a panel and a core of the panel exceeds a threshold value; a first surface of the sacrificial layer is adhered to the pull stub by way of a first adhesive interface and a second surface of the sacrificial layer is adhered to the faceskin of the panel by way of a second adhesive interface;
the bond strength is expected to exceed a specified maximal FWT load; and
the sacrificial layer is configured such that separation of any one or more of the first adhesive interface, the second adhesive interface and the sacrificial layer occurs only at a tensile load that is (i) greater than the threshold value and (ii) less than the specified maximal FWT load.

11. The apparatus of claim 10, wherein the FWT test apparatus is a pneumatic adhesion tensile testing instrument.

12. The apparatus of claim 10, wherein the sacrificial layer is a double sided tape.

13. The apparatus of claim 12, wherein the double-sided tape has a modulus of less than 500.

14. The apparatus of claim 12, wherein the double-sided tape has a modulus of approximately 75.

15. The apparatus of claim 10, wherein the panel is a spacecraft solar array panel or equipment panel.

16. The apparatus of claim 10, wherein the faceskin is aluminum or carbon composite.

17. The apparatus of claim 10, wherein the pull stub has a test article interface area defined by a perimeter and the pull stub is configured to have a first stiffness proximate to the perimeter and a second stiffness in a central region of the test article interface area, the first stiffness being substantially less than the second stiffness.

18. The apparatus of claim 10, wherein the pull stub is configured to have a first thickness proximate to the perimeter and a second thickness in a central region of the test article interface area, the first thickness being substantially less than the second thickness.

* * * * *